(12) United States Patent
Roensch et al.

(10) Patent No.: US 6,761,872 B2
(45) Date of Patent: *Jul. 13, 2004

(54) METHOD FOR GENERATING CHLORINE DIOXIDE

(75) Inventors: L. Fred Roensch, Glen Allen, VA (US); Richard H. Tribble, Richmond, VA (US); Dick Hilliard, Glen Allen, VA (US)

(73) Assignee: ChemTreat, Inc., Glen Allen, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/179,201

(22) Filed: Jun. 26, 2002

(65) Prior Publication Data

US 2003/0003015 A1 Jan. 2, 2003

Related U.S. Application Data

(62) Division of application No. 09/814,927, filed on Mar. 23, 2001, now Pat. No. 6,436,345.

(51) Int. Cl.[7] .............................................. C01B 11/02
(52) U.S. Cl. ............................ 423/477; 422/28; 422/37
(58) Field of Search .......................... 423/477; 422/28, 422/37

(56) References Cited

U.S. PATENT DOCUMENTS

| | | |
|---|---|---|
| 3,591,515 A | 7/1971 | Lovely |
| 4,247,531 A | 1/1981 | Hicks |
| 4,414,193 A | 11/1983 | Fredette et al. |
| 4,547,381 A | 10/1985 | Mason et al. |
| 4,585,482 A | 4/1986 | Tice et al. |
| 4,590,057 A | 5/1986 | Hicks |
| 4,683,039 A | 7/1987 | Twardowski et al. |
| 4,689,169 A | 8/1987 | Mason et al. |
| 4,861,514 A | 8/1989 | Hutchings |
| 4,986,990 A | 1/1991 | Davidson et al. |
| 5,031,700 A | 7/1991 | McDougall et al. |

(List continued on next page.)

FOREIGN PATENT DOCUMENTS

| | | |
|---|---|---|
| CA | 1 264 659 | 1/1990 |
| EP | 0 448 659 B1 | 1/1997 |

OTHER PUBLICATIONS

Aieta et al., "Determination of Chlorine Dioxide, Chlorine, Chlorite, and Chlorate in Water," Research and Technology, Jan. 1984, pp. 64–70.

Aieta et al., "Chlorine Dioxide Chemistry: Generation and Residual Analysis," Symposium on Chemistry and Chemical Analysis of Water Intended for Reuse, 179th National Meeting of the Amer. Chem. Soc., Houston, TX, Mar. 1980, pp. 1–22.

Masschelein et al., "Chlorine Dioxide—Chemistry and Environmental Impact of Oxchlorine Compounds," Ann Arbor Science Publishers, Inc., 1979, pp. 1–191.

*Primary Examiner*—Robert J. Warden, Sr.
*Assistant Examiner*—Sean E. Conley
(74) *Attorney, Agent, or Firm*—Harness, Dickey & Pierce, P.L.C.

(57) ABSTRACT

The present invention provides a new method for the in situ generation of chlorine dioxide from a solution of sodium chlorite and carbon dioxide. The present invention produces effective levels of chlorine dioxide without having to resort to the use of hydrochloric acid, sulfuric acid, hydrogen peroxide, chlorine, sulfur dioxide, or methanol. By eliminating the use of toxic and/or hazardous compounds, the present invention provides a safer means for generating and using chlorine dioxide in a wider variety of applications than previously possible. For instance, the present invention can easily be adapted for the treatment of combustion exhaust gases, flue gases, cooling towers, chilled water systems, contaminated groundwater, and agricultural produce or products.

17 Claims, 3 Drawing Sheets

U.S. PATENT DOCUMENTS

| | | |
|---|---|---|
| 5,091,107 A | 2/1992 | Hutchings |
| 5,110,580 A * | 5/1992 | Rosenblatt et al. ......... 423/472 |
| 5,126,070 A | 6/1992 | Leifheit et al. |
| 5,158,658 A | 10/1992 | Cawlfield et al. |
| 5,234,678 A | 8/1993 | Rosenblatt et al. |
| 5,378,447 A | 1/1995 | Jackson et al. |
| 5,567,405 A | 10/1996 | Klatte et al. |
| 5,651,996 A | 7/1997 | Roozdar |
| 5,674,466 A | 10/1997 | Dahl et al. |
| 5,676,920 A | 10/1997 | Lipsztajn |
| 5,719,100 A * | 2/1998 | Zahradnik et al. .......... 502/417 |
| 5,770,171 A | 6/1998 | Sundblad et al. |
| RE36,064 E * | 1/1999 | Davidson et al. ........... 424/665 |
| 5,922,776 A | 7/1999 | Wellinghoff et al. |
| 5,980,826 A | 11/1999 | Barenberg et al. |
| 6,436,345 B1 * | 8/2002 | Roensch et al. .............. 422/37 |

* cited by examiner

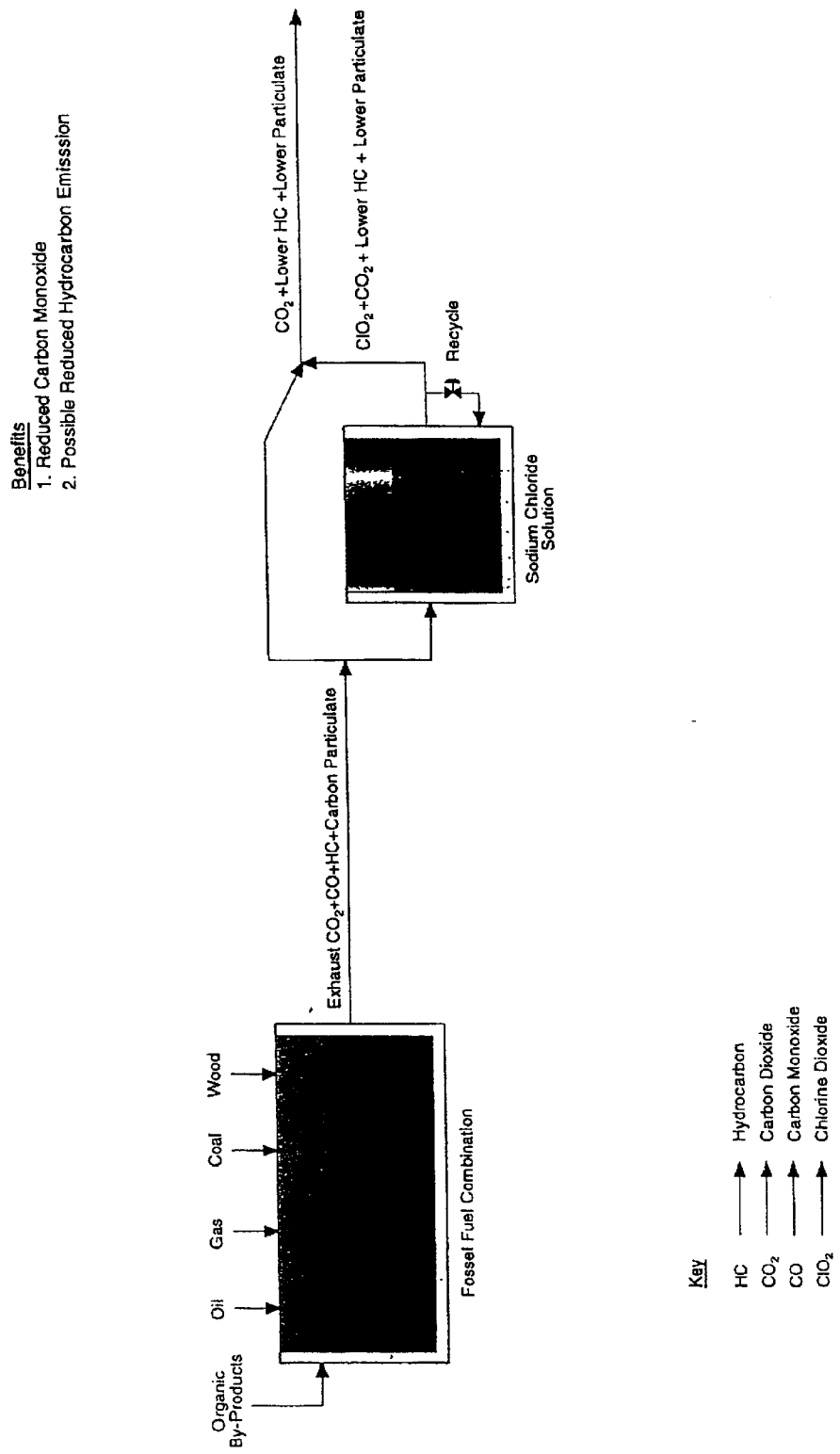

METHOD FOR GENERATING CHLORINE DIOXIDE

This invention relates to a method and apparatus for generating chlorine dioxide using carbon dioxide and sodium chlorite and is a divisional of application Ser. No. 09/814,927 filed Mar. 23, 2001 now U.S. Pat. No. 6,436,345 B1, which issued Aug. 20, 2002, the entire contents of which are incorporated by reference.

BACKGROUND OF THE INVENTION

1. Field of the Invention

Chlorine dioxide is a strong oxidizer and is widely used as a bleaching and/or disinfectant agent, with hundreds of tons being generated and used each day in the paper and water treatment industries. Chlorine dioxide is also used in considerably smaller quantities in treating agricultural produce and certain medical applications. Chlorine dioxide is well known as an algaecide, fungicide, germicide, deodorant, bleach, and general antiseptic. Currently, the equipment required for generating chlorine dioxide usually requires gaseous chlorine, sulfuric acid, or a combination of sodium hypochlorite (bleach) and acid with either sodium chlorite or sodium chlorate. Because one or more hazardous materials are typically required to generate the chlorine dioxide or produced as a byproduct, the use of chlorine dioxide has been somewhat limited. The cost of chlorine dioxide generating units and the need for trained personnel to operate and maintain the generating units has also hampered the wider utilization of chlorine dioxide. Accordingly, there exists a need for a method that is capable of readily and safely producing chlorine dioxide without requiring the use of more hazardous chemicals or generating them as reaction byproducts.

2. Background Art

Chlorine dioxide is a hazardous material. Pure chlorine dioxide is an oily, dark amber liquid and is extremely unstable at temperatures above −40° C. Chlorine dioxide is also explosively unstable as a gas in concentrations greater than 10% by volume in air or at partial pressures above 76 mm Hg (1.46 psig). Above these levels chlorine dioxide may detonate if it contacts flammable organic solvents or other oxidizable materials. Chlorine dioxide is also pressure sensitive and may decompose violently if compressed, making it impractical to store or ship. Pure solutions of chlorine dioxide may also detonate if exposed to bright light or an ignition source such as heat, a spark, or an open flame. The upper boundary for safe chlorine dioxide concentrations in aqueous solutions is about 8 g/L at 30° C., with most generating systems being designed to operate well below that limit, typically producing solutions having 1–3 g/L chlorine dioxide.

It is well known that chlorine dioxide is formed by reaction of sodium chlorite and an acid. For instance, U.S. Pat. No. 3,591,515 to Lovely teaches the use of various acidifying agents to generate chlorine dioxide at pH levels below 6 and form a dry powder fungicide. U.S. Pat. No. 4,330,531 to Alliger discloses a twin-compartment container for generating chlorine dioxide by reacting solutions of lactic acid and sodium chlorite. U.S. Pat. No. 4,585,482 to Tice, et al. discloses a biocidal composition that uses a chlorine dioxide-liberating compound and a hydrolyzable organic acid-generating polymer (such as a methylvinylether/maleic anhydride copolymer) for lowering the pH of the composition and slowly releasing the chlorine dioxide.

Chlorine dioxide is generally formed in one of two ways, either by reducing a chlorate ion ($ClO_3^-$) in an acidic medium according to reaction [1]:

$$ClO_3^- + 2H^+ + e^- \rightarrow ClO_2 + H_2O \quad [1]$$

or by oxidizing a chlorite ion ($ClO_2^-$) according to reaction [2].

$$ClO_2^- \rightarrow ClO_2 + e^- \quad [2]$$

The choice of reducing agent for chlorine dioxide generation from chlorate has a great bearing on optimum reaction conditions, byproducts, and economics. Production from chlorite ion ($ClO_2^-$) is rather uneconomical. Indeed reaction [2] is reversible and chlorite is commonly synthesized from chlorine dioxide. Reducing agents typically used for producing chlorine dioxide from chlorate are sulfur dioxide ($SO_2$), methanol ($CH_3OH$), chloride ion ($Cl^-$), and hydrogen peroxide ($H_2O_2$). The associated half reactions are represented by reactions [3]–[6].

$$SO_2 + 2H_2O \rightarrow SO_4^{-2} + 4H^+ + 2e^- \quad [3]$$

$$CH_3OH + H_2O \rightarrow HCOOH + 4H^+ + 4e^- \quad [4]$$

$$2Cl^- \rightarrow Cl_2 + 2e^- \quad [5]$$

$$H_2O_2 \rightarrow O_2 + 2H^+ + 2e^- \quad [6]$$

Combining reaction [1] with reactions [3]–[6] produces reactions [7]–[10].

$$2ClO_3^- + SO_2 \rightarrow 2ClO_2 + SO_4^{-2} \quad [7]$$

$$4ClO_3^- + CH_3OH + 4H^+ \rightarrow 4ClO_2 + HCOOH + 3H_2O \quad [8]$$

$$ClO_3^- + Cl^- + 2H^+ \rightarrow ClO_2 + Cl_2 + H_2O \quad [9]$$

$$2ClO_3^- + H_2O_2 + 2H^+ \rightarrow 2ClO_2 + O_2 + 2H_2O \quad [10]$$

The byproducts formed are sulfate ion ($SO_4^{2-}$), formic acid (HCOOH), chlorine ($Cl_2$), and oxygen ($O_2$). The acid equivalents required per mole of chlorine dioxide produced differ and are zero for sulfur dioxide, one for methanol, two for chloride, and one for hydrogen peroxide. Acid consumption is also influenced by the process conditions used in particular commercial designs.

In all systems, a side reaction may occur, reduction of chlorate to chloride according to reaction [11].

$$ClO_3^- + 6H^+ + 6e^- \rightarrow Cl^- + 3H_2O \quad [11]$$

Steps must be taken to minimize this reaction by careful choice and control of reaction conditions. The basic mechanism of chlorine dioxide formation has been extensively studied and has previously been described in detail elsewhere by Haller and Northgraves in *TAPPI* (a publication of the Technical Association of the Pulp and Paper Industry) (April 1955) and Lenzi and Rapson in the *Pulp Paper Magazine of Canada* (1962). In each of the disclosed mechanisms, chloride plays a crucial role as evidenced by its presence in all chlorate-based reaction media and by the trace amounts of chlorine in the chlorine dioxide formed. No chlorine dioxide is formed if chloride ion is not present in the reaction medium. Chloride ion is introduced into the system by reduction of chlorate to chloride (reaction [11] above) or by addition of chloride in the feed. In a 1956 *TAPPI* article, Rapson proposed the following mechanism where chloride ion is the reducing agent.

$$HClO_3+HCl \rightarrow HClO_2+HClO \qquad [12]$$

$$HClO_3+HClO_2 \rightarrow 2ClO_2+H_2O \qquad [13]$$

$$HClO+HCl \rightarrow Cl_2+H_2O \qquad [14]$$

The formation of byproducts, other than those identified in reactions [7]–[10], is governed by the chlorate salt and acid selected. In all commercial processes, the chlorate salt used is sodium chlorate ($NaClO_3$) and, to date, the most commonly used acids have been sulfuric ($H_2SO_4$) and hydrochloric (HCl). Consequently, the most common byproducts are sodium sulfate ($Na_2SO_4$) and sodium chloride (NaCl). Depending upon process conditions, sulfate is recovered as neutral crystalline sodium sulfate, sodium sesquisulfate ($Na_3H(SO_4)_2$), or is dissolved in an acidic effluent. If hydrochloric acid is used, sodium chloride is recovered in a crystalline form or in an internally recycled solution.

Commercial chlorine dioxide generation systems can be broadly divided into atmospheric and sub-atmospheric processes. Atmospheric processes include the Mathieson, Solvay, and Rapson R2 processes which use sulfur dioxide, methanol, and sodium chloride, respectively, as the primary reducing agents. Each of the processes use air to strip and dilute the chlorine dioxide and have an overflow of spent sulfuric acid. In the 1950s, the Mathieson process was dominant, followed by the Solvay process. The Mathieson process was developed in 1950 by Olin-Mathieson Chemical Corporation and generated chlorine dioxide by reducing sodium chlorate with sulfur dioxide in the presence of sulfuric acid.

The Mathieson process chemistry generally follows reaction [7] above, i.e.

$$2NaClO_3+SO_2 \rightarrow 2ClO_2+Na_2SO_4 \qquad [15]$$

However under low acidity conditions an unwanted side reaction, reflected in reactions [3] and [11] above, can considerably reduce the yield.

$$NaClO_3+3SO_2+3H_2O \rightarrow NaCl+3H_2SO_4 \qquad [16]$$

In order to suppress this side reaction, an excess of sulfuric acid is typically fed to a Mathieson-type generator to create a 450–500 g/L acid concentration (9–10 N $H_2SO_4$). The acid (typically 2–2.5 tons of acid per ton of $ClO_2$ produced) overflows from the generator and must be recovered and used elsewhere or, less preferably, neutralized and discharged. Some unreacted sodium chlorate also leaves the generator with the acid. The loss of the sodium chlorate and the contribution of reaction [16] typically limits the yield of a Mathieson-type generator to less than 90%.

The Solvay process uses methanol as the reducing agent and, like the Mathieson process, typically utilizes a 450–500 g/L sulfuric acid solution. The primary reaction, based on reaction [8], can be written as shown in reaction [17].

$$4NaClO_3+H_2SO_4+CH_3OH \rightarrow 4ClO_2+2Na_2SO_4+\\ HCOOH+3H_2O \qquad [17]$$

Both the Mathieson and Solvay processes are capable of producing chlorine dioxide solutions having low chlorine concentrations.

By the 1960s, the growing recognition of the crucial role of the chloride ion in chlorine dioxide synthesis processes had led to the increasing use of Rapson's R2 process. The overall reaction in the R2 process, based on reaction [9] can be represented by reaction [18].

$$2NaClO_3+2NaCl+2H_2SO_4 \rightarrow 2ClO_2+Cl_2+2Na_2SO_4+2H_2O \qquad [18]$$

The R2 process, like the Mathieson process, is also subject to an unwanted side reaction, based on reactions [6] and [11], resulting in the production of chlorine according to reaction [19].

$$NaClO_3+5NaCl+3H_2SO_4 \rightarrow 3Cl_2+3H_2O+3Na_2SO_4^+ \qquad [19]$$

As can be seen in reactions [18] and [19], the R2 process generates chlorine, typically in a 0.6:1 weight ratio with the desired $ClO_2$. A portion of the chlorine, approximately 1 g/L of chlorine, usually remains in the chlorine dioxide solution with the balance being separated and used to produce sodium hypochlorite. Because the R2 reaction is much faster than the Mathieson or Solvay reaction, the process can be carried out in a single vessel. However, because the R2 reaction does not form the in situ acid of the Mathieson and Solvay processes, and because additional water is needed as the result of the addition of sodium chloride, the addition of approximately 4.5 ton of acid per ton of $ClO_2$ is required for the R2 process, which limits its practicality for many industrial locations, particularly in areas where water consumption is an issue.

In response to the need to decrease the amount of waste acid produced, efforts were made to find methods of crystallizing or recycling the sodium sulfate from the waste acid. One solution was the application of an evaporator-crystallizer that could function as a chlorine dioxide generator with the steam and vacuum serving to control chlorine dioxide partial pressure. This led to the development of the R3/SVP process in which the basic R2 chemistry was performed under vacuum, at higher temperatures, and in the presence of proprietary catalysts, to achieve suitable production rates and yields with a reaction solution at acidities below 4.5 N $H_2SO_4$, the point below which neutral anhydrous sodium sulfate can be crystallized and filtered. The R3/SVP process also produced byproduct chlorine, typically in about the same 0.6:1 ratio as the R2 process, with $ClO_2$ and about 2 g/L of $Cl_2$ remaining in the chlorine dioxide solution and with the balance again being separated and used to produce chlorine water or hypochlorite.

As pulp mills decreased sodium and sulfur losses and also increased their use of chlorine dioxide, the amount of sodium/sulfur byproducts formed exceeded the pulp mills' needs. Further, the use of byproduct chlorine to produce hypochlorite also became less attractive as mills worked toward obtaining both higher brightness pulps and suppressing or eliminating chloroform formation. These conditions and demands led to processes using hydrochloric acid as a replacement for part or all of the sulfuric acid in an R3 or SVP process (see reaction [20] below). The hydrochloric acid could either be purchased or made by burning byproduct chlorine with hydrogen in a hydrochloric acid burner, or alternatively, the chlorine could be reacted with sulfur dioxide and water to make a mixture of hydrochloric and sulfuric acids (see reaction [21] below). These changes, along with the partial replacement of sulfuric acid, significantly reduced the byproduct sodium sulfate and virtually eliminated the chlorine water and hypochlorite byproducts.

$$2NaClO_3+2HCl+H_2SO_4 \rightarrow 2ClO_2+Na_2SO_4+Cl_2 \qquad [20]$$

$$Cl_2+SO_2+2H_2O \rightarrow 2HCl+H_2SO_4 \qquad [21]$$

Hydrochloric acid processes can be operated independently or integrated with an onsite chlorate plant. The key reactions are the production of chlorine dioxide according to reaction [22] with sodium chlorate being produced by electrolysis of the byproduct salt according to reaction [23].

$$2NaClO_3 + 4HCl \rightarrow ClO_2 + 2Cl_2 + 2H_2O + 2NaCl \quad [22]$$

$$NaCl + 3H_2O \rightarrow NaClO_3 + 3H_2 \quad [23]$$

The byproduct chlorine from the generator and supplemental chlorine are then reacted with the byproduct hydrogen from the chlorate reaction to produce HCl according to reaction [24], producing an overall stoichiometry for the integrated process, i.e., the combination of reactions [22]–[24], as reflected in reaction [25].

$$Cl_2 + H_2 \rightarrow 2HCl \quad [24]$$

$$Cl_2 + 4H_2O \rightarrow 2ClO_2 + 4H_2 \quad [25]$$

This integrated process produces no sodium sulfate and requires chlorine input in a weight ratio of approximately 0.7:1 to that of the product $ClO_2$ (reaction [24]) to make the necessary quantity of hydrochloric acid and help balance the $NaOH/Cl_2$ needs. The integrated process does, however, increase the space and capital requirements compared with other alternative chlorine dioxide plants.

The interest in eliminating byproduct chlorine, decreasing byproduct sodium sulfate, and improving the overall efficiency and production rate in turn led to the development of an alternative methanol-based process. The overall reaction for this R8/SVP Methanol (MeOH) process can be represented by reaction [26].

$$3NaClO_3 + 2H_2SO_4 + 0.80CH_3OH \rightarrow 3ClO_2 + Na_3H(SO_4)_2 + 2.3H_2O + 0.8HCOOH \quad [26]$$

The reaction represented in reaction [26] does not take into account the smaller amounts of methanol which typically leave the generator in the gas phase and/or dissolved in the chlorine dioxide solution. Some of the formic acid (HCOOH) reacts further according to reaction [27].

$$HCOOH \rightarrow CO_2 + 2H^+ + 2e^- \quad [27]$$

Because formic acid has a similar vapor pressure to that of water, most of it is stripped from the generator. A typical 10 g/L $ClO_2$ solution will also contain 0.2–0.9 g/L of $CH_3OH$, 1.7 g/L of CHOOH, 0.4 g/L of $CO_2$, and 0.1 g/L of $Cl_2$. Because the R8/SVP MeOH processes typically operate at acidities above 5 N, sodium and sulfate are recovered as sodium sesquisulfate ($Na_3H(SO_4)_2$). This process has the advantages of virtually eliminating the chlorine byproduct (0.1 g/L of $Cl_2$ in a 10 g/L solution of $ClO_2$), producing less salt cake than the R3/SVP processes, increasing chlorine dioxide yield to over 95%, and improving production capacity. The residual chlorine is a product of the low concentration of chloride ions in the generator. If this low concentration of chloride ions is eliminated, the production of chlorine dioxide ceases, and the reactor enters a condition known as "white-out" in which the reactor generates a toxic white gas (comprising primarily chlorine and water vapor) and a grayish-white generator liquor. Maintaining lower acidities (approximately 5–7 N) helps maintain a sufficient concentration of chloride ions but results in decreased efficiency of methanol use. Alternatively, operation at higher acidities (approximately 8–10 N) leads to more efficient methanol use, but additional steps, including perhaps the addition of sodium chloride, are typically added to guard against a white-out condition.

When hydrogen peroxide is used as the reducing agent the overall reaction based on reaction [9] can be represented reaction [29].

$$2NaClO_3 + H_2O_2 + H_2SO_4 \rightarrow 2ClO_2 + O_2 + 2H_2O + Na_2SO_4 \quad [29]$$

The use of hydrogen peroxide as the reducing agent has the advantage of producing no byproduct chlorine and directly producing neutral sodium sulfate, but the relatively high cost of hydrogen peroxide has limited its widespread use.

Efforts have also been made to develop various electrochemical processes which can split the salt cake byproduct and/or the sodium chlorate feed into their respective acids and bases according to reactions [30] and [31].

$$Na_2SO_4 + 2H_2O \rightarrow 2NaOH + H_2SO_4 \quad [30]$$

$$NaClO_3 + H_2O \rightarrow NaOH + HClO_3 \quad [31]$$

The electrochemical processes, however, are not yet cost-competitive with the more traditional chemical processes so their adoption tends to be driven more strongly by environmental pressures or restrictions relating to plant discharges and disposals.

Although not discussed here in detail, those of skill in the art will be familiar with a wide variety of alternative processes for generating chlorine dioxide including:

The Modified Mathieson process in which small amounts of sodium chloride (NaCl) were added to the reactants in the primary generator to improve the reduction efficiency of the chlorate and increase generator capacity.

The Hoist process which is a batch process similar to the Mathieson process with the significant difference being found in the solution concentrations and the batch-wise operation.

The Kesting Day-Fenn, or Day-Kesting, process utilizes hydrochloric acid (HCl) for reducing $NaClO_3$ and is suitable for integration with an electrolytic plant for the production of chlorate.

The R1 process, the first of the "R" processes developed by Dr. Howard Rapson, relied on reacting sodium chlorate and sodium chlorite in a strong acid to form chlorine dioxide.

The R2 process used a mixture of $NaClO_3$, $H_2SO_4$, and NaCl for reducing the chlorate, thereby eliminating the need for $SO_2$. The R2 process, however, increased the formation of chlorine ($Cl_2$) which was then absorbed (usually to form sodium hypochlorite (NaOCl)) after the $ClO_2$ absorption tower.

The R2H process replaced NaCl and half of the $H_2SO_4$ used in the R2 process with hydrochloric acid (HCl).

The R3 process was another modified R2 process in which the reaction temperatures are increased to boiling and concentrations increased strengthened to permit crystallization of sodium sulfate ($Na_2SO_4$) in the reaction vessel. This process, commercialized as the R3 process by Erco Ltd. (now a part of Sterling Pulp Chemicals, Ltd.) and as the SVP process by the Hooker Chemical Company (now Eka-Nobel), is also sometimes referred to as the "effluent-free" process because since the byproduct removed is crystalline $Na_2SO_4$.

The R3H process, like the R2H process, replaced the NaCl and half of the $H_2SO_4$ of the R3 process with HCl.

The R5 process is basically the same as the R3 process with the exception that the NaCl and all of the $H_2SO_4$ are replaced with HCl, leaving HCl and $NaClO_3$ as the only feed streams into the generator with the byproduct being crystalline NaCl suitable for reuse in chlorate manufacture. Further, the R5 process is distinguished from the R2 process by the higher operating temperatures and concentrations that permit the recovery of the crystalline byproduct and incorporates technology developed by Dow Chemical Canada.

The R6 process was an "integrated" process used in conjunction with an electrolytic plant producing $NaClO_3$. Variations of this basic "integrated" process are also known as the Lurgi integrated process or the Chemetics integrated process.

The R7 process was another modification of the R3 process in which chlorine gas from the exit stream was reacted with $SO_2$ to form a mixed acid of $H_2SO_4$ and HCl that is then returned to the generator. The only substantial byproduct of the R7 process is anhydrous $Na_2SO_4$.

The R8 process utilizes methanol as the reducing agent and produces an acid salt, sodium sesquisulfate [$Na_3H(SO_4)_2$], as a byproduct. The sodium sesquisulfate must then be neutralized with caustic soda before recovery in the liquor system.

The R9 process is an extension of the R8 process in which the sodium sesquisulfate is diluted with water and separated into caustic soda and sulfuric acid in a membrane cell.

The R10 process is another extension of the R8 process in which the sodium sesquisulfate is diluted with both water and methanol following removal of sodium sulfate in a second filtration stage with the filtrate being returned to the generator.

The R11 process, uses hydrogen peroxide as the reducing agent for $ClO_2$ generation. This process has seen limited use due to the higher operating costs associated with hydrogen peroxide.

The R12 process electrochemically converts sodium chlorate to a mixed feed of sodium chlorate and chloric acid ($HClO_3 \cdot 7H_2O$) which is fed to the $ClO_2$ generator, which proportionally reduces sodium sulfate formation, while producing sodium hydroxide as a by-product.

The R13 process, uses chloric acid from the R12 process to produce $ClO_2$ without the byproduct $Na_2SO_4$.

The SVP-Lite process is another methanol based process similar in some respects to the R8 process. The main difference between the SVP-Lite and R8 processes is the acid strength in the generator.

The SVP-HP process is similar to SVP-Lite except that it utilizes hydrogen peroxide rather than methanol for reducing the chlorate, is operated at subatmospheric pressures, and produces as its byproduct neutral sodium sulfate ($Na_2SO_4$).

The SVP-HPA process is an atmospheric process that is similar to the SVP-HP process in that it also utilizes hydrogen peroxide and produces $Na_2SO_4$ as a byproduct. In addition to the $Na_2SO_4$, the reactor also produces a spent acid stream.

The Lurgi process is an integrated process similar to the R6 and Chemetics processes in which an onsite electrolytic process is used to produce $ClO_2$ from chlorine and water. The hydrogen produced is reacted with $Cl_2$ to form HCl, which is, in turn, used in the process. Additional $Cl_2$ is required to provide sufficient HCl for the process.

The Chemetics process is another integrated process similar to the R6 and Lurgi processes.

An alternative to the chlorate-based $ClO_2$ synthesis is the chlorite-based synthesis. In the chlorite-based synthesis, a chlorite solution, typically sodium chlorite, is mixed with an acid to form an unstable chlorous acid, which in turn, disproportionates into chlorine dioxide according to reactions such as [32]–[34].

$$NaClO_2 + HCl \rightarrow HClO_2 + NaCl \quad [32]$$

$$HClO_2 + 3HCl \rightarrow 2Cl_2 + 2H_2O \quad [33]$$

$$4NaClO2 + 2Cl2 \rightarrow 4ClO2 + 4NaCl \quad [34]$$

The resulting overall reaction corresponds to reaction [35].

$$5NaClO_2 + 4HCl \rightarrow 4ClO_2 + 5NaCl + 2H_2O \quad [35]$$

Although with simple mixing the initial chlorite is eventually consumed, the yield of $ClO_2$ tends to be lower than expected, typically 60–80% depending on the starting proportions of the chlorite and acid reactants. Indeed, a concurrent reaction appears to be reflected by reaction [36].

$$4NaClO_2 + 2HCl \rightarrow 2ClO_2 + NaClO_3 + 3NaCl + H_2O \quad [36]$$

As a result of reaction [36] and other competing side reactions, the $ClO_2$ produced tends to be impure and contain both chlorine and chlorate. The most common industrial applications rely on hydrochloric acid, sulfuric acid, and acetic acid, with hydrochloric acid being the most widely used. Catalysts for this family of reaction include sodium peroxide, potassium perborate, and cobalt sulfate. Typically yields are improved by running the synthesis with excess acid, typically about 300%, to increase the synthesis yields to levels approaching 100% (i.e., 4 moles of $ClO_2$ produced from 5 moles of $NaClO_2$). A much less frequently used synthesis described in Swiss patent 481,839 (1970) relies on a combination of powdered $NaClO_2$ and powdered citric acid that are dissolved in 1.5 liters of water to produce a solution having about 5 g $ClO_2$ in a solution of citric acid.

Chlorite can also be reacted with chlorine to produce $ClO_2$ according to reaction [37].

$$2NaClO_2 + Cl_2 \rightarrow 2NaCl + 2ClO_2 \quad [37]$$

However, implementing this synthesis using solid chlorite and gaseous chlorine introduces contact problems such as the chlorite becoming coated with salt and local heating that increases the danger of an explosion. As a result, it is common to implement this reaction in solution under subatmospheric conditions to reduce the danger of explosion.

BRIEF SUMMARY OF THE INVENTION

It is an object of the present invention to provide an improved method for the generation of aqueous chlorine dioxide solutions using as reactants only carbon dioxide gas and sodium chlorite that can implemented with less complex apparatus and with greater safety.

It is a further object of the present invention to produce chlorine dioxide in an aqueous system without adding corrosive ions such as sulfate and chloride.

It is a further object of the present invention to produce chlorine dioxide in an aqueous system without increasing the dissolved solids.

It is a further object of the present invention to produce chlorine dioxide in an aqueous system while reducing the potential for calcium carbonate scaling.

It is a further object of the present invention to produce chlorine dioxide in an aqueous system to reduce organic stack emissions.

It is a further object of the present invention to produce chlorine dioxide in an aqueous system for treatment of ground water contamination including, but not limited to, phenols, bacteria, manganese, and iron.

It is a further object of the present invention to produce chlorine dioxide in an aqueous system for conversion of hydrogen sulfide into hydrogen sulfate.

It is a further object of the present invention to provide a method for generating an aqueous solution of chlorine dioxide or a gaseous mixture including chlorine dioxide suitable for the treatment of agricultural products including leaf products such as tobacco, root crops such as potatoes, and other fruits and vegetables.

BRIEF DESCRIPTION OF THE DRAWINGS

FIG. 3 is a representation of the application of the present invention for treatment of the exhaust stream generated by the combustion of organic fuels in which the carbon dioxide from the exhaust stream is utilized in the production of chlorine dioxide.

DETAILED DESCRIPTION OF THE INVENTION

As reflected in the discussion above, there are many methods for generating chlorine dioxide. Each of the prior art methods, however, either requires the use of a strong acid or other oxidizer, produces unwanted byproducts, or is prohibitively expensive. The present invention resolves the deficiencies of the prior art methods by utilizing as the primary reactants only a solution of sodium chlorite and carbon dioxide gas to produce chlorine dioxide.

Figure 1:
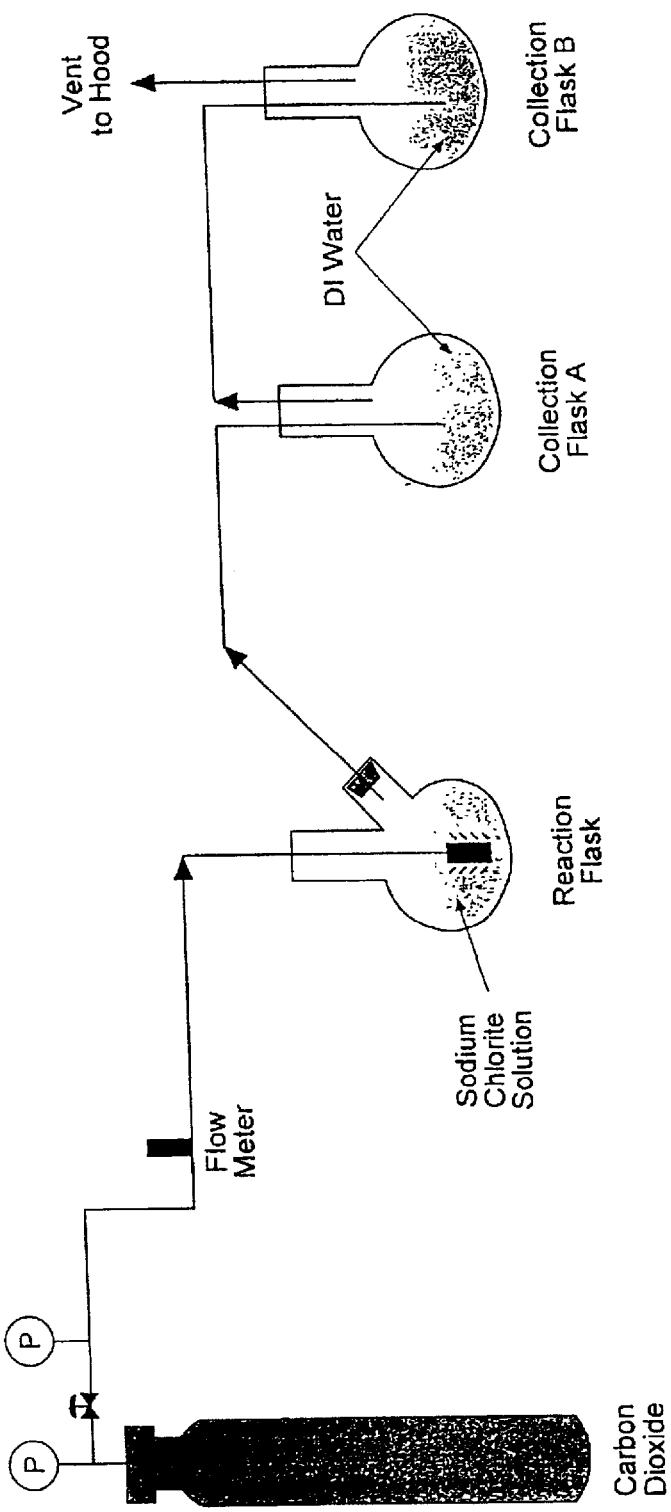
FIG. 1 is a representation of the experimental apparatus used to confirm the utility of the present invention and includes a carbon dioxide source, a flow meter, a reaction flask holding a sodium chlorite solution and a series of two collection flasks initially filled with deionized water ("DI water").

Using the apparatus illustrated in FIG. 1, gaseous carbon dioxide was injected into a solution of sodium chlorite to produce chlorine dioxide that was, in turn, captured in the first and second collection flasks. The volume of sodium chlorite used was 100 ml of a 10% sodium chlorite solution having an initial pH of 9–10. It was found that the chlorine dioxide yield from a conventional sodium chlorite solution, typically stabilized with carbonate at a pH of about 11.8–12.4, could be improved by at least partially removing the stabilizing carbonate. It was found that sufficient carbonate removal was achieved by adding 500 g of calcium chloride to one liter of 10% sodium chlorite to remove a portion of the carbonate and lower the solution pH to approximately 10.2.

It appears that during the carbon dioxide injection step, the formation of carbonic acid begins to lower the pH of the sodium chlorite solution. The formation of chlorine dioxide begins when the pH of the sodium chlorite solution becomes slightly acidic, e.g., when the pH reached about 6.0–5.0 In the experimental apparatus, the sodium chlorite solution pH tended to stabilize at a value between 4 and 6 after about two minutes of carbon dioxide injection. If desired, the initial pH could also be partially reduced with another acid, such as acetic or citric acid, to hasten the production of chlorine dioxide with the injection of carbon dioxide. In most instances, however, it is believed that the carbon dioxide injection alone will be sufficient to accomplish the aims of the present invention.

Several stoichiometric reactions have been proposed for the acid activation of a chlorite solution. The two stoichiometric reactions most widely accepted are:

$$4ClO_2^- + 4H^+ \rightarrow 2ClO_2 + Cl^- + ClO_3^- + 2H^+ + H_2O \quad [38]$$

$$5ClO_2^- + 5H^+ \rightarrow 4ClO_2 + HCl + 2H_2O \quad [39].$$

The source of acid in the claimed method is the formation of carbonic acid when carbon dioxide is dissolved in water:

$$CO_2 + H_2O \rightarrow H_2CO_3 \rightarrow H^+ + HCO_3^- \quad [40].$$

Using the experimental apparatus illustrated in FIG. 1, optimal collection of chlorine dioxide was achieved by initially injecting carbon dioxide into the sodium chlorite solution for ten minutes followed with a ten-minute incubation period (during which no further carbon dioxide was added). Thereafter, the carbon dioxide injection was resumed for periods of two minutes, each injection period followed by another ten-minute incubation period. The first one-liter collection flask was then removed and the chlorine dioxide levels measured after each gas injection period and changed to a fresh flask. Total carbon dioxide injection periods have ranged from 30 minutes to almost seven hours using a nominal carbon dioxide injection rate of 5 SCFH.

Based on the applicants' experimental work, it does not appear that constant gas flow is necessary. Indeed, it was found that having a period of carbon dioxide injection followed by an incubation period (during which no carbon dioxide was injected) helps prevent loss of chlorine dioxide into the atmosphere. With incubation times included, experiments have been run up to almost seven hours without exhausting the initial charge of sodium chlorite solution.

EXAMPLE 1

The results for Example 1 provided in Table 1 below were generated using one initial 10-minute gas exposure and seven 2-minute periods of carbon dioxide injection, followed by seven 10-minute incubation periods. To maximize chlorine dioxide collection, both first and second collection flasks were used in series.

TABLE 1

|  | $ClO_2$ | $ClO_2^-$ | $ClO_3^-$ |
|---|---|---|---|
| Reaction Flask: | 606 mg/L | 23.02 g/L | 1.73 g/L |
| Collection Flask 1: | 19 mg/L | 26 mg/L | 2.1 mg/L |
| Collection Flask 2: | 19 mg/L | 19 mg/L | 2.7 mg/L |

EXAMPLE 2

Using the same conditions as in Example 1, a second experiment was run to produce the results provided in Table 2.

TABLE 2

|  | $ClO_2$ | $ClO_2^-$ | $ClO_3^-$ |
|---|---|---|---|
| Reaction Flask: | 523 mg/L | 86.90 g/L | 4.16 g/L |
| Collection Flask 1: | 5 mg/L | 99 mg/L | 5.9 mg/L |
| Collection Flask 2: | 5 mg/L | 98 mg/L | 5.9 mg/L |

Although minor amounts of chlorate were detected in the collection flasks, the applicants believe that the chlorate detected may have been the result of the disproportion decomposition reaction between the time the sample as collected and the time when the sample was analyzed.

Additional experiments were then conducted to explore the impact of treating the initial sodium chlorite solution to remove a portion of the calcium carbonate.

EXAMPLE 3

Starting with a commercially available 25% sodium chlorite solution having up to 5% alkalinity, a test solution of 10% sodium chlorite and not more than 2% alkalinity was prepared. The starting pH of the non-neutralized solution was approximately 11.7 and the temperature was approximately 21° C. Table 3 represents data collected with varying incubation periods, each followed by a 2 minute period of $CO_2$ injection at 5 scf/hour (142 liters/hour), for a total test time of 95 minutes. The $CO_2$ injection lowered the solution pH from the initial 11.7 to between 5.6 and 5.7 and maintained the pH within this range for the duration of the experiment.

TABLE 3

| Incubation Time (minutes) | Collection Flask $ClO_2$ concentration (mg/L) | Reaction Flask pH |
|---|---|---|
| 2 | 0.2 | 5.6 |
| 2 | 0.8 | 5.7 |
| 2 | 1.2 | 5.6 |
| 2 | 1.5 | 5.6 |
| 2 | 1.8 | 5.6 |
| 5 | 1.7 | 5.6 |
| 10 | 5.1 | 5.6 |
| 10 | 6.2 | 5.6 |
| 20 | 10.8 | 5.6 |
| 20 | 11.7 | 5.7 |
| Total 75 | 41 | |

Over the 95 minute duration of the experiment, 41 milligrams of chlorine dioxide was generated from the 10% sodium chlorite solution.

EXAMPLE 4

Starting with the same commercially available 25% sodium chlorite solution having up to 5% alkalinity, a test solution of 10% sodium chlorite with the alkalinity adjusted to 3% was prepared. The starting pH of the non-neutralized solution was approximately 11.7 and the temperature was approximately 21° C. Table 4 represents data collected with varying incubation periods, each followed by a 2 minute period of $CO_2$ injection at 5 scf/hour (142 liters/hour), for a total test time of 95 minutes. The $CO_2$ injection lowered the solution pH from the initial 11.7 to between 5.7 and 5.9 for the duration of the experiment. As reflected in Table 4, despite the increased alkalinity, the injected $CO_2$ was able to form sufficient carbonic acid both to lower the pH and to produce slightly decreased amount of $ClO_2$ (i.e., 36.8 mg.).

TABLE 4

| Incubation Time (minutes) | Collection Flask $ClO_2$ concentration (mg/L) | Reaction Flask pH |
|---|---|---|
| 2 | 0.2 | 5.8 |
| 2 | 0.4 | 5.7 |
| 2 | 0.9 | 5.8 |
| 2 | 0.9 | 5.8 |
| 2 | 1.3 | 5.8 |
| 5 | 1.9 | 5.8 |
| 10 | 4.2 | 5.9 |
| 10 | 4.8 | 5.9 |
| 20 | 9.9 | 5.8 |
| 20 | 12.3 | 5.8 |
| Total 75 | 36.8 | |

EXAMPLE 5

Starting with the same commercially available 25% sodium chlorite solution having up to 5% alkalinity, a test solution of 10% sodium chlorite that also included a minor portion of sodium carbonate was prepared and treated with calcium chloride to form a calcium carbonate precipitate and then filtered to remove substantially all of the calcium carbonate. The starting pH of the neutralized solution was approximately 11.7 and the temperature was approximately 21° C. Table 5 represents data collected with varying incubation periods, each followed by a 2 minute period of $CO_2$ injection at 5 scf/hour (142 liters/hour), for a total test time of almost 8 hours. The $CO_2$ injection lowered the solution pH from the initial 11.7 to between 4.4 and 4.7 over the course of the experiment. As reflected in Table 5, despite the increased alkalinity, the injected $CO_2$ was able to form sufficient carbonic acid to maintain the lower pH level and to continue to produce $ClO_2$ over the course of the experiment for a total of approximately 284 mg. in Flask 1 and Flask 2.

TABLE 5

| Temperature (° C.) | Incubation Time (minutes) | pH | $ClO_2$ Flask 1 (mg/L) | $ClO_2$ Flask 2 (mg/L) |
|---|---|---|---|---|
| 21 | 2 | 4.7 | 0.5 | 0.0 |
| 21 | 2 | 4.5 | 0.7 | 0.1 |
| 21 | 2 | 4.5 | 1.5 | 0.1 |
| 21 | 5 | 4.5 | 1.7 | 0.1 |
| 21 | 5 | 4.4 | 1.7 | 0.1 |
| 21 | 5 | 4.5 | 2.9 | 0.2 |
| 25 | 5 | — | 5.6 | 0.4 |
| 25 | 5 | — | 5.1 | 0.5 |
| 25 | 10 | — | 7.6 | 0.7 |
| 25 | 10 | — | 7.8 | 0.9 |
| 25 | 10 | — | 7.6 | 0.9 |
| 25 | 10 | — | 7.7 | 0.9 |
| 25 | 20 | — | 10.1 | 1.3 |
| 25 | 20 | — | 10.6 | 1.1 |
| 25 | 20 | — | 10.4 | 1.2 |
| 25 | 20 | — | 11.0 | 1.1 |
| 25 | 20 | — | 10.6 | 1.2 |
| 30–33 | 20 | — | 12.4 | 1.1 |
| 30–33 | 20 | — | 12.9 | 1.1 |
| 30–33 | 20 | — | 14.0 | 1.5 |
| 30–33 | 20 | — | 12.6 | 1.6 |
| 30–33 | 20 | — | 13.1 | 1.7 |
| 30–33 | 20 | — | 14.6 | 1.8 |
| 30–33 | 20 | — | 12.9 | 1.6 |
| 30–33 | 20 | — | 11.7 | 1.3 |
| 30–33 | 20 | — | 11.2 | 1.2 |
| 30–33 | 20 | — | 12.7 | 1.1 |
| 30–33 | 20 | — | 12.3 | 1.8 |
| 30–33 | 20 | 4.6 | 12.5 | 1.9 |
| Total | 409 | | 255.5 | 28.5 |

Figure 2:
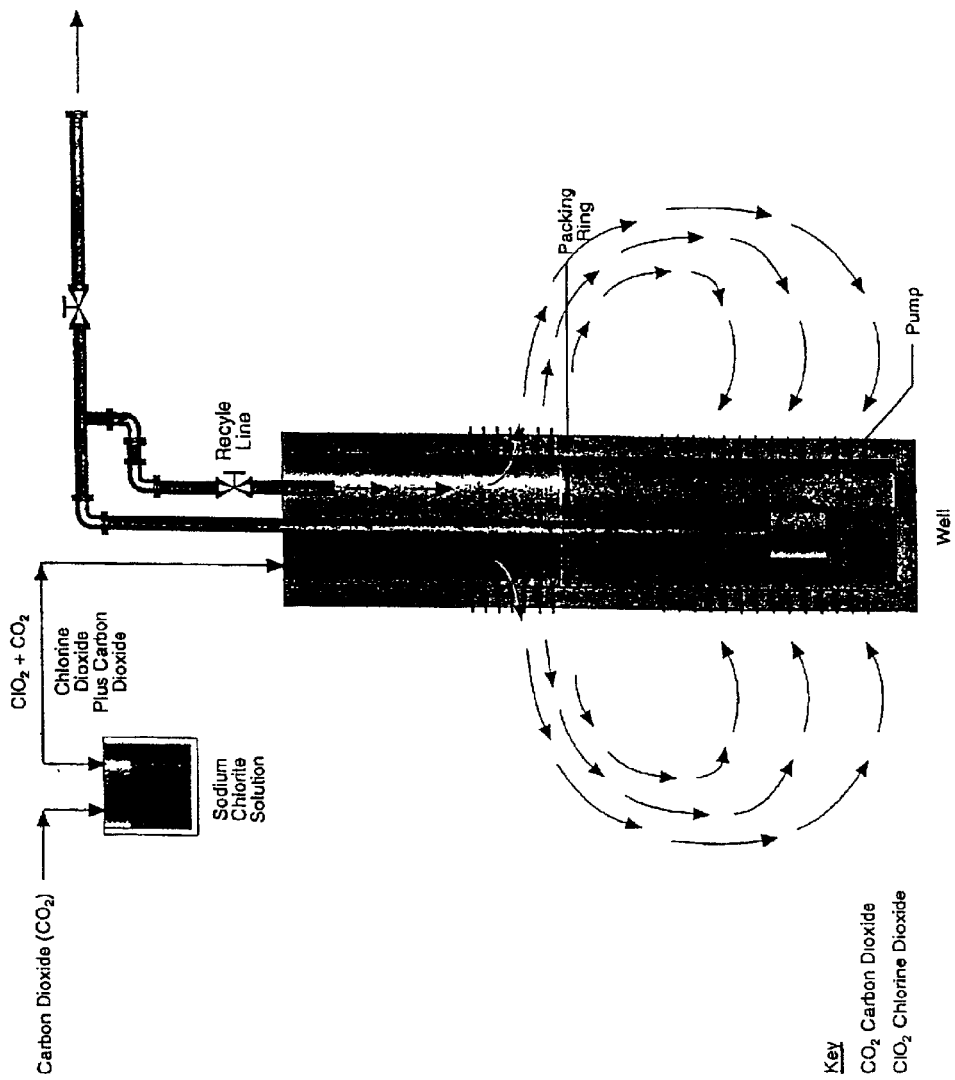
FIG. 2 is a representation of the application of the present invention for treatment of a contaminated well and surrounding groundwater.

As illustrated in FIGS. 2 and 3, the basic chlorine dioxide generator constructed and operated according to the invention can be used to create and/or supply low-level aqueous solutions of chlorine dioxide in a variety of applications including treatment of exhaust streams from organic fuel combustion or in situ ground water treatment.

As shown in FIG. 2, a chlorine dioxide generator according to the present invention can be used to generate and supply a gaseous mixture of $ClO_2$ and $CO_2$ to well water for the treatment of organic or bacterial contamination. In the alternative, the $ClO_2$ and $CO_2$ stream can be mixed with a well water stream to form a slightly acidic chlorine dioxide solution that is then injected into the well.

As shown in FIG. 3, a significant component of the exhaust stream is carbon dioxide. As a result, a portion of the exhaust stream can be passed through a sodium chlorite solution to generate the desired chlorine dioxide. It is preferred that in instances in which the sodium chlorite solution also includes sodium carbonate the sodium chlorite:sodium carbonate ratio be maintained at a value of at least 5:1. The remaining portion of the exhaust stream can also be combined with a chlorine dioxide solution according to known methods downstream of the chlorine dioxide generator to treat the exhaust further, thereby reducing both the hydrocarbon and particulate content of the exhaust stream.

Although particular preferred embodiments of the invention have been disclosed in detail for illustrative purposes, it will be recognized by those of ordinary skill in the art that certain variations or modifications to the disclosed method lie within the scope of the invention as defined by the following claims.

We claim:

1. A method of producing chlorine dioxide comprising the steps of:

forming an aqueous reaction solution of sodium chlorite, the reaction solution having an initial pH greater than 7;

passing carbon dioxide gas through the reaction solution;

reacting a portion of the carbon dioxide gas to form carbonic acid in the reaction solution;

lowering the pH of the reaction solution to a pH of less than about 5.5;

forming chlorine dioxide; and removing a mixed gas stream including carbon dioxide and chlorine dioxide from the reaction solution.

2. A method for producing chlorine dioxide according to claim 1, wherein the step of forming the aqueous solution of sodium chlorite further comprises the step of removing a majority of any carbonate present in the reaction solution.

3. A method for producing chlorine dioxide according to claim 2, wherein the step of removing a majority of the carbonate present in the reaction solution further comprises adding sufficient calcium chloride to precipitate calcium carbonate and removing the calcium carbonate from the reaction solution.

4. A method for producing chlorine dioxide according to claim 1, wherein the sodium chlorite solution has a sodium chlorite:sodium carbonate ratio of not less than 5:1.

5. A method for producing chlorine dioxide according to claim 1, wherein the step of passing carbon dioxide gas through the reaction solution includes passing a combustion exhaust stream through the reaction solution.

6. A method for producing chlorine dioxide according to claim 1, further comprising:

passing the mixed gas stream through water to form a collection solution that includes chlorine dioxide and is substantially free of sodium chlorite.

7. A method for producing chlorine dioxide according to claim 6, wherein the collection solution has a pH of less than about 7.

8. A method for producing chlorine dioxide according to claim 6, wherein the pH of the reaction solution is lowered to a value of between about 4.4 and 6.0 during the step of forming the chlorine dioxide.

9. A method for producing chlorine dioxide according to claim 6, wherein the reaction solution includes at least about 10% sodium chlorite.

10. A method for producing chlorine dioxide according to claim 1, further comprising:

combining the mixed gas stream with a contaminated gas stream to form a treated gas stream.

11. A method for producing chlorine dioxide according to claim 10, wherein the contaminated gas stream is a combustion exhaust stream.

12. A method for producing chlorine dioxide according to claim 1, wherein the step of passing carbon dioxide gas through the reaction solution and the step of forming chlorine dioxide are substantially simultaneous.

13. A method for producing chlorine dioxide according to claim 12, wherein the step of passing carbon dioxide gas through the reaction solution occurs under a pressure of about one atmosphere.

14. A method for producing chlorine dioxide according to claim 12, wherein the step of passing carbon dioxide gas includes injecting a substantially constant volume of carbon dioxide gas through the reaction solution during the step of forming chlorine dioxide.

15. A method for producing chlorine dioxide according to claim 12, wherein the step of passing carbon dioxide gas further comprises:

injecting carbon dioxide into the reaction solution for a first period;

incubating the reaction solution for a second period during which substantially no additional carbon dioxide is injected into the reaction solution; and injecting carbon dioxide into the incubated reaction solution for a third period.

16. A method for producing chlorine dioxide according to claim 15, wherein:

the first period is between about 2 minutes and 10 minutes;

the second period is between about 2 minutes and about 20 minutes; and the third period is about 2 minutes.

17. A method for producing chlorine dioxide according to claim 15, wherein the step of passing carbon dioxide gas further comprises the steps of:

a) injecting carbon dioxide into the reaction solution for a first period;

b) incubating the reaction solution for a second period during which substantially no additional carbon dioxide is injected into the reaction solution; and c) injecting carbon dioxide into the incubated reaction solution for a third period; and repeating steps b) and c) at least once.

* * * * *